United States Patent [19]

Matsumoto

[11] Patent Number: 5,637,606
[45] Date of Patent: Jun. 10, 1997

[54] HAIR GROWER BASED ON ALLANTOIN OR DERIVATIVES THEREOF

[76] Inventor: Toshihiro Matsumoto, Haimu-Uenohara 201, 645, Matsudome, Uenoharamachi, Kitatsuru-gun, Yamanashi 409-01, Japan

[21] Appl. No.: 456,516

[22] Filed: Jun. 1, 1995

[30] Foreign Application Priority Data

Jun. 10, 1994 [JP] Japan ................................... 6-163416
Mar. 10, 1995 [JP] Japan ................................... 7-089932

[51] Int. Cl.⁶ ................................................. A61K 31/415
[52] U.S. Cl. ......................... 514/389; 424/70.1; 514/880; 514/881
[58] Field of Search .............................. 514/389, 880, 514/881; 424/701

[56] References Cited

U.S. PATENT DOCUMENTS 4,814,351  3/1989  Mathews et al. .......................... 514/566
5,214,041  5/1993  Ishino et al. .......................... 514/223.5
5,215,995  6/1993  Honbo et al. ............................ 514/291

FOREIGN PATENT DOCUMENTS 56-18040   5/1981   Japan .
60-87208   5/1985   Japan .
4-360834   12/1992  Japan .

OTHER PUBLICATIONS

Current Therapy, 1984, pp. 559–603.

*Primary Examiner*—Shelley A. Dodson
*Attorney, Agent, or Firm*—Armstrong, Westerman, Hattori, McLeland & Naughton

[57] ABSTRACT

The present invention provides a hair grower which prevents loss of hair, promoted hair development and cures alopecia, comprising as an active ingredient one or more of the following compounds: allantoin, derivatives thereof, compounds thereof and compounds of allantoin derivatives and optionally further comprising as an active ingredient one or more aluminum compounds.

1 Claim, No Drawings

HAIR GROWER BASED ON ALLANTOIN OR DERIVATIVES THEREOF

BACKGROUND OF THE INVENTION

1. Field of the Invention

This invention relates to a novel hair grower which is excellent in preventing loss of hair as well as promoting hair growth.

2. Description of the Prior Art

With respect to the mechanisms of hair loss and hair development, many aspects are still unknown. In addition, many aspects are also left unknown in the physiological mode of action of hair growth promoting components involved in hair loss and hair development. At present, it is considered that loss of hair is attributable to endocrine disorders, autonomic imbalance, blood circulation disorders, malnutrition and so forth. Among all, excessive androgen levels and blood circulation disorders in the scalp are the two causes most strongly supported. The androgen theory is based on the facts that mature age alopecia (baldness) does not occur in males who have removed their testes, that alopecia of this type is not found in healthy females, and that this type alopecia is caused in females by the injection of androgens. However, androgen receptors have not been found in neither hair roots nor trichogen cells, and thus the androgen theory is unable to explain the mechanism of the occurrence of hair loss sufficiently. On the other hand, the theory of blood circulation disorders explains the cause of hair loss as follows: blood circulation disorders which are attributable to a scalp tension caused by a relatively small scalp compared to the size of cranial bones results in the lowering of the metabolic function in hair bulbs as well as the function in trichogen cells.

A number of hair growers have been known in the art which are prepared by combining various components with pharmaceutical effects. Such components with pharmaceutical effects include logwood (*Haematoxylon campechianum*) extract, pyrimidine-N-oxide derivatives, the extract of *Rosa rugosa* Thunb. var. plena Regel, etc. as an androgen repressor; Japanese green gentian extract, vitamin E, acetylcholine derivatives, *Fomes japonicus* extract, garlic extract, minoxidil, etc. as a peripheral vasodilator/blood circulation promoter; capsicum tincture, cantharis tincture, ginger tincture, mint oil, camphor, etc. as a local stimulant; urea, Mini-Sasanishiki (a variety of rice) extract, etc. as a moisture-retaining agent; 1-menthol, aloe extract, diphenhydramine hydrochloride, etc. as an antiphlogistic/anti-pruritic; 1-dioxide derivatives, sodium oxalate, quercetin, pirolinic N-oxide, N-methyl-L-serine, *Illicium religiosum* extract, etc. as a trichogen/hair-grower; salicylic acid, etc. as a keratolytic.

Although the mechanism of the occurrence of hair loss has not been elucidated completely by any of the existing theories as described above, it is clear that the direct cause of hair loss is the lowering of functions in trichogen cells. Therefore, if a mecidine effectively works in trichogen cells and thereby restore their normal functions, it would become possible to prevent hair loss and promote hair development. From this point of view, various activating agents for hair roots and trichogen cells have been used. These agents include glyceride pentadecanoate, prostaglandin, ginkgo leaf extract, fatty acids with carbon atoms in odd numbers and derivatives thereof (Japanese Unexamined Patent Publications Nos. 61-5007 and 61-5014), branched fatty acids and derivatives thereof (Japanese Unexamined Patent Publication No. 61-7205), and so on.

The effects which all of the above-mentioned components have been expected to produce are the prevention of hair loss, promotion of hair development, prevention of hair thinning, growth of hair, prevention of dandruff and itching, keeping the scalp clean, keeping the scalp and hair healthy, and a sense of refreshment when applied. Conventional hair growers which are prepared by combining the above-mentioned components are so constituted that a suitable combined use or continuous use of them will produce a hair growing effect.

OBJECTS AND SUMMARY OF THE INVENTION

Conventional hair growers containing those pharmaceutically effective components, however, have not been able to achieve satisfactory effects in prevention and inhibition of dandruff, itching and hair falling, as well as promotion of hair development and growth. Accordingly, development of a hair grower which has even stronger effects in both prevention of hair loss and promotion of hair growth is needed.

Under the circumstances, it is the object of the present invention to provide a novel hair loss-preventive hair grower having a remarkable hair-growing effect which prevents hair loss, dandruff and itching, and promotes hair growth.

Toward the achievement of the above object, the present inventors have examined hair-growing effects of various compounds in human bodies in vivo. As a result of this survey and confirmation experiments, it has been found that allantoin, derivatives thereof, compounds thereof and compounds of allantoin derivatives have an excellent hair-growing action without causing any adverse effect upon the hair or scalp. In addition, as a result of further extensive and intensive research, it has been found that allantoin, derivatives thereof, compounds thereof and compounds of allantoin derivatives reveal a more efficient and stronger trichogenous effect when they are jointly used with an aluminium compound. The present invention have been accomplished based on these findings.

Thus, in one aspect of the present invention, there is provided a hair grower comprising as an active ingredient(s) one (a single compound) or more compounds (mixed compound of 2 or more species) selected from the group consisting of allantoin, derivatives thereof, compounds thereof and compounds of allantoin derivatives. By the application of such active ingredients to scalp cells, trichogen cells are activated, and thus hair development is realized.

In another aspect of the present invention, there is provided a hair grower comprising as an active ingredient(s) one (a single compound) or more compounds (mixed compound of 2 or more species) selected from the group consisting of allantoin, derivatives thereof, compounds thereof and compounds of allantoin derivatives, and further comprising as an active ingredient(s) one (a single compound) or more compounds (mixed compounds of 2 or more species) selected from aluminium compounds. These active ingredients combined together achieve a still stronger trichogeneous effect based on the interaction of regeneration of trichogen cells, stimulation of hair roots, and promotion of blood circulation in the scalp.

DETAILED DESCRIPTION OF THE INVENTION

With respect to the derivative of allantoin to be used in the present invention, for example, allantoin chlorohydroxyaluminium and allantoin dihydroxyaluminium may be enumerated. Other allantoin derivatives may also be used in the hair grower of the present invention. With respect to the aluminium compound to be used in the present invention, for example, aluminium lactate and aluminium hydroxide may be enumerated. Other aluminium compounds may also be used in the hair grower of the present invention.

Initially, allantoin was found in a secretion from bovine allantois, after which this substance was named. It is known that allantoin and derivatives thereof remove necrotized tissues, activate skin cells, lyse keratin, and enhance the absorption of other drugs. They have no skin irritation, and it has been confirmed that they have no toxicity or adverse effects upon organisms. Furthermore, as a result of a vivisection using rat, it was reconfirmed that allantoin and derivatives thereof have no adverse effect [see footnotes in Nippon Official Book Association (ed.), Standards for Raw Materials of Cosmetics, 2nd Version].

In the hair grower of the present invention, there may be used allantoin or a derivative thereof to which other chemically active group (such as K, Ag, Hg, Bi, Al, Cd, Zn, Pb, Cu and other chemical substances) is added. Therefore, the hair grower of the present invention is not particularly limited, except that it contains one (a single compound) or more compounds (mixed compound of 2 or more species) selected from the group consisting of allantoin, derivatives thereof, compounds obtained by adding some other group to allantoin and compounds obtained by adding some other group to allantoin derivatives. The amounts of these compounds in the hair grower may be varied depending on the form of use, and not particularly limited. In principle, these compounds may be contained in effective amounts. Generally, the compound can reveal a hair-growing effect when the content in the total amount of the hair grower as a final product is 0.0003 mol or more allantoin groups per 100 g, preferably 0.001 mol or more allantoin groups per 100 g. For example, in the case of allantoin whose molecular weight is 158, it is effective when the content in the total amount of the hair grower as a final product is about 0.05 g or more per 100 g; preferably, the content is about 0.16 g or more per 100 g. With respect to the alminium compound, the compound is effective when the content in the total amount of the hair grower as a final product is 0.0003 mol or more alminium per 100 g, preferably 0.001 mol or more per 100 g. For example, in the case of aluminium lactate whose molecular weight is 294, it is effective when the content in the total amount of the hair grower as a final product is about 0.1 g or more per 100 g; preferably, the content is about 0.3 g or more per 100 g. These active ingredients (i.e., allantoin, derivatives thereof, compounds thereof and compounds of allantoin derivatives, and aluminium compounds) become more effective as their concentrations increase, and the upper limit for these contents is not provided (see Tables 1 and 2).

Allantoin and derivatives thereof are known to be extremely stable [see footnotes in Nippon Official Book Association (ed.), Standards for Raw Materials of Cosmetics, 2nd Version]. Accordingly, the hair grower of the present invention is extremely stable, and is applicable to various cosmetic products such as a hair cream, milky lotion, hair liquid, hair lotion, hair rinse, hair tonic, pomade, shampoo, soap and so on by combining the hair grower with various known cosmetic bases.

The effect of the hair grower of the present invention can be detected by applying the hair grower solution of a specified concentration to the scalp of a male or female with conditions of hair loss or alopecia for a certain period of time, and measuring the hairs grown.

The hair grower comprising as an active ingredient(s) one or more compounds selected from the group consisting of allantoin, derivatives thereof, compounds thereof and compounds of allantoin derivatives has an action of reactivating trichogen cells. With this action, the hair grower achieves the hair-growing effect that will convert the downy hair-like hairs covering the part which lost hairs into initial, long and thick hairs.

The hair grower comprising as an active ingredient(s) one or more compounds selected from the group consisting of allantoin, derivatives thereof, compounds thereof and compounds of allantoin derivatives, and further comprising as an active ingredient(s) one or more compounds selected from aluminium compounds has (i) the action of reactivating trichogen cells based on the former active ingredient(s); (ii) a scalp-stimulating action caused by the astriction upon trichogen cells based on the latter active ingredient(s); and (iii) an action of growing the subcutaneous tissue of the scalp and recovering the initial scalp neuropil which reacts with stimulation properly, based on the interaction of (i) and (ii) above. This hair grower can achieve a strong hair-growing effect that will convert the downy hair-like hairs covering the part which lost hairs into initial, long and thick hairs.

PREFERRED EMBODIMENTS OF THE INVENTION

Now the present invention will be described more specifically below with reference to the following Examples and Comparative Examples, which should not be contrued as limiting the scope of the present invention.

(1) Allantoin and Derivatives Thereof

Commercial products may be used. The allantonin derivative to be used in the present invention includes, for example, allantoin chlorohydroxyaluminium and allantoin dihydroxyaluminium. Other allantoin derivatives may also be used in the hair grower of the present invention as active ingredients.

(2) Aluminium Compounds

Commercial products may be used. The alminium compound to be used in the present invention includes, for example, alminium lactate and alminium hydroxide. Other alminium compounds may also be used in the hair grower of the present invention as active ingredients.

(3) Various Preparation Examples

Preparation example for shampoo (i)

| Components: | (Content in % by weight) |
|---|---|
| Sodium polyoxyethylele alkyl ether sulfate (E · O 2 mol) | 15 |
| Palm oil fatty acid diethanolamide | 5 |
| Glycerol | 3 |
| Allantoin | 0.4 |
| Perfume and antiseptic | Proper quantity |
| Deionized water | An amount to make the total 100 |

Preparation example for shampoo (ii)

| Components: | (Content in % by weight) |
|---|---|
| Sodium polyoxyethylele alkyl ether sulfate (E · O 2 mol) | 15 |

-continued

| Components: | (Content in % by weight) |
|---|---|
| Palm oil fatty acid diethanolamide | 5 |
| Glycerol | 3 |
| Allantoin chlorohydroxyalminium | 0.4 |
| Perfume and antiseptic | Proper quantity |
| Deionized water | An amount to make the total 100 |

Preparation example for hair cream (i)

| Components: | (Content in % by weight) |
|---|---|
| Liquid paraffin | 20 |
| Solid paraffin | 3 |
| Polyoxyethylele cetyl ether (E · O 15 mol) | 2 |
| Sorbitan sesquioleate | 1 |
| Allantoin | 0.4 |
| Aluminium hydroxide | 0.8 |
| Glycerol | 3 |
| Perfume and antiseptic | Proper quantity |
| Deionized water | An amount to make the total 100 |

Preparation example for hair cream (ii)

| Components: | (Content in % by weight) |
|---|---|
| Liquid paraffin | 20 |
| Solid paraffin | 3 |
| Polyoxyethylele cetyl ether (E · O 15 mol) | 2 |
| Sorbitan sesquioleate | 1 |
| Allantoin | 0.4 |
| Potassium hydroxide | 0.1 |
| Glycerol | 3 |
| Perfume and antiseptic | Proper quantity |
| Deionized water | An amount to make the total 100 |

Preparation example for hair lotion (i)

| Components: | (Content in % by weight) |
|---|---|
| 95% ethanol | 60 |
| Glycerol | 3 |
| Polyoxyethylele-sorbitan mololaurate (E · O 20 mol) | 1 |
| Allantoin chlorohydroxyalminium | 0.4 |
| Aluminium lactate | 0.8 |
| Perfume and antiseptic | Proper quantity |
| Deionized water | An amount to make the total 100 |

Preparation example for hair lotion (ii)

| Components: | (Content in % by weight) |
|---|---|
| 95% ethanol | 60 |
| Glycerol | 3 |
| Polyoxyethylele-sorbitan mololaurate (E · O 20 mol) | 1 |
| Allantoin | 0.4 |
| Perfume and antiseptic | Proper quantity |
| Deionized water | An amount to make the total 100 |

Preparation example for hair tonic (i)

| Components: | (Content in % by weight) |
|---|---|
| 95% ethanol | 60 |
| Polyoxyethylele hardened castor oil (E · O 60 mol) | 0.5 |
| Glycerol | 3 |
| Allantoin chlorohydroxyalminium | 0.4 |
| Perfume and antiseptic | Proper quantity |
| Deionized water | An amount to make total 100 |

Preparation example for hair tonic (ii)

| Components: | (Content in % by weight) |
|---|---|
| 95% ethanol | 60 |
| Polyoxyethylele hardened castor oil (E · O 60 mol) | 0.5 |
| Glycerol | 3 |
| Allantoin dihydroxyalminium | 0.4 |
| Perfume and antiseptic | Proper quantity |
| Deionized water | An amount to make the total 100 |

Preparation example for pomade (i)

| Components: | (Content in % by weight) |
|---|---|
| Japanese wax | 13 |
| Castor oil | 86.5 |
| Allantoin | 0.4 |
| Aluminium lactate | 0.8 |
| Perfume | Proper quantity |

Preparation example for pomade (ii)

| Components: | (Content in % by weight) |
|---|---|
| Japanese wax | 13 |
| Castor oil | 86.5 |
| Allantoin or a compound thereof | 0.4 |
| Perfume | Proper quantity |

(4) Testing of the Hair-Growing Effect of the Hair Grower of the Present Invention

EXAMPLE 1

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin chlorohydroxyalminium | 0.5 g |
| Perfume and antiseptic | Proper quantity |
| Deionized water | An amount to make the total 100 g |

EXAMPLE 2

A hair tonic of the following composition was used.

| Components: | (Content) |
| --- | --- |
| Ethanol | 60 ml |
| Vegetable oil | 0.5 g |
| Propylene glycol | 5.0 g |
| Allantoin | 0.5 g |
| Deionized water | An amount to make the total 100 ml |

COMPARATIVE EXAMPLE 1

A shampoo of the following composition was used.

| Components: | (Content) |
| --- | --- |
| Sodium lauryl ether sulfate | 20.0 g |
| Triethanol amine lauryl sulfate | 5.0 g |
| Propylene glycol | 2.0 g |
| Perfume and antiseptic | Proper quantity |
| Deionized water | An amount to make the total 100 g |

COMPARATIVE EXAMPLE 2

A hair tonic of the following composition was used.

| Components: | (Content) |
| --- | --- |
| Ethanol | 60 ml |
| Vegetable oil | 0.5 g |
| Propylene glycol | 5.0 g |
| Deionized water | An amount to make the total 100 ml |

Forty male subjects suffering from mature age alopecia were divided into 4 groups, each consisting of 10 subjects. Two groups received the test solutions shown in above Examples, and the other two the test solutions shown in above Comparative Examples. Trichogram test and test on the ratio of conversion into grown-up hair were performed in these 4 groups.

Trichogram Test

Before and after application of the above-mentioned test solutions, the roots of pulled out hairs were examined with a microscope. The number of telogen (rest stage) hair roots were counted based on the morphology of hair roots. The hair-growing effect of individual test solution was compared with each other based on increase or decrease in the ratio of telogen hair roots. "Telogen hair root" means the root of a hair whose growth has been stopped. Since those who suffer from alopecia have more telogen hair roots than normal individuals, the hair-growing effect was evaluated based on a decrease in these telogen hair roots. Each test solution was applied to the scalp for 3 months continuously. Immediately before the commencement of the application and immediately after the completion of the application, 30 hairs per subject were pulled out respectively, and their hair roots were examined. The results are shown in Table 1.

TABLE 1

Results of Trichogram Test

| Group | Ratio of telogen hair roots | Ratio of subjects | Evaluation of hair-growing effect |
| --- | --- | --- | --- |
| EXAMPLE 1 | Decrease by 20% or more | 60% | Effective |
|  | ±20% | 40% |  |
|  | Increase by 20% or more | 0% |  |
| EXAMPLE 2 | Decrease by 20% or more | 60% | Effective |
|  | ±20% | 30% |  |
|  | Increase by 20% or more | 10% |  |
| COMPARATIVE EXAMPLE 1 | Decrease by 20% or more | 10% | Not effective |
|  | ±20% | 80% |  |
|  | Increase by 20% or more | 10% |  |
| COMPARATIVE EXAMPLE 2 | Decrease by 20% or more | 10% | Not effective |
|  | ±20% | 70% |  |
|  | Increase by 20% or more | 20% |  |

Test on the Ratio of Conversion into Grown-up Hair

In each of the 40 subjects suffering from male pattern alopecia, 3 spots in the scalp covered with downy hairs were examined before and after the application of the above-mentioned test solutions, and the ratios of convertion into grown-up hairs were compared. "Grown-up hair" used herein means any hair except downy hair, i.e. a hair which has a length of at least 14 mm. The conversion from downy hairs into grown-up hairs directly reflects the hair-growing effect. Immediately before the commencement of the application and immediately after the completion of a 6-month application, the above-mentioned spots covered with downy hairs were directly photographed, and the conversion ratio was calculated. The ratio of conversion into grown-up hair is expressed as a mean value in percent of the three spots. The results are shown in Table 2.

TABLE 2

Test on the Ratio of Convertion into Grown-up Hair

| Group | Mean grown-up hair conversion ratio | Evaluation of hair-growing effect |
| --- | --- | --- |
| EXAMPLE 1 | 12.7% | Effective |
| EXAMPLE 2 | 10.3% | Effective |
| COMPARATIVE EXAMPLE 1 | 1.1% | Not effective |
| COMPARATIVE EXAMPLE 2 | 1.7% | Not effective |

EXAMPLE 3

A shampoo of the following composition was used.

| Components: | (Content) |
| --- | --- |
| Sodium lauryl ether sulfate | 20.0 g |
| Triethanol amine lauryl sulfate | 5.0 g |
| Propylene glycol | 2.0 g |
| Allantoin | 0.5 g |
| Perfume and antiseptic | Proper quantity |
| Deionized water | An amount to make the total 100 g |

EXAMPLE 4

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin | 10.0 g |
| Perfume and antiseptic | Proper quantity |
| Deionized water | An amount to make the total 100 g |

EXAMPLE 5

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin | 20.0 g |
| Perfume and antiseptic | Proper quantity |
| Deionized water | An amount to make the total 100 g |

EXAMPLE 6

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin | 0.5 g |
| Aluminium lactate | 1.0 g |
| Perfume and antiseptic | Proper quantity |
| Deionized water | An amount to make the total 100 g |

EXAMPLE 7

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin | 10.0 g |
| Aluminium lactate | 10.0 g |
| Perfume and antiseptic | Proper quantity |
| Deionized water | An amount to make the total 100 g |

EXAMPLE 8

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Allantoin | 20.0 g |
| Aluminium lactate | 20.0 g |
| Perfume and antiseptic | Proper quantity |
| Deionized water | An amount to make the total 100 g |

COMPARATIVE EXAMPLE 3

A shampoo of the following composition was used.

| Components: | (Content) |
|---|---|
| Sodium lauryl ether sulfate | 20.0 g |
| Triethanol amine lauryl sulfate | 5.0 g |
| Propylene glycol | 2.0 g |
| Perfume and antiseptic | Proper quantity |
| Deionized water | An amount to make |

Seventy male subjects suffering from mature age alopecia were divided into 7 groups, each consisting of 10 subjects. Groups 1 to 6 received the individual test solutions shown in above Examples, and Group 7 the test solution shown in above Comparative Example. Trichogram test and test on the ratio of conversion into grown-up hair were performed in a similar manner as described above. The results of these tests are shown in Table 3 and Table 4, respectively.

TABLE 3

Results of Trichogram Test

| Group | Ratio of telogen hair roots | Ratio of subjects | Evaluation of hair-growing effect |
|---|---|---|---|
| EXAMPLE 3 | Decrease by 20% or more | 50% | Effective |
| | ±20% | 50% | |
| | Increase by 20% or more | 0% | |
| EXAMPLE 4 | Decrease by 20% or more | 60% | Effective |
| | ±20% | 40% | |
| | Increase by 20% or more | 0% | |
| EXAMPLE 5 | Decrease by 20% or more | 60% | Effective |
| | ±20% | 40% | |
| | Increase by 20% or more | 0% | |
| EXAMPLE 6 | Decrease by 20% or more | 80% | Effective |
| | ±20% | 20% | |
| | Increase by 20% or more | 0% | |
| EXAMPLE 7 | Decrease by 20% or more | 90% | Effective |
| | ±20% | 10% | |
| | Increase by 20% or more | 0% | |
| EXAMPLE 8 | Decrease by 20% or more | 90% | Effective |
| | ±20% | 10% | |
| | Increase by 20% or more | 0% | |
| COMPARATIVE EXAMPLE 3 | Decrease by 20% or more | 10% | Not effective |
| | ±20% | 80% | |
| | Increase by 20% or more | 10% | |

TABLE 4

Test on the Ratio of Conversion into Grown-up Hair

| Group | Mean grown-up hair conversion ratio | Evaluation of hair-growing effect |
|---|---|---|
| EXAMPLE 3 | 10.7% | Effective |
| EXAMPLE 4 | 11.3% | Effective |

TABLE 4-continued

Test on the Ratio of Conversion into Grown-up Hair

| Group | Mean grown-up hair conversion ratio | Evaluation of hair-growing effect |
| --- | --- | --- |
| EXAMPLE 5 | 11.7% | Effective |
| EXAMPLE 6 | 16.3% | Effective |
| EXAMPLE 7 | 19.7% | Effective |
| EXAMPLE 8 | 22.3% | Effective |
| COMPARATIVE EXAMPLE 3 | 1.3% | Not effective |

Similar results were obtained when the hair grower of the present invention was used as a base for other cosmetic products, such as hair tonic.

Other Qualitative Phenomena

The following are the remarkable effects observed in the results of the clinical tests on mature age alopecia performed in the above Examples.

Degree of hair loss improvement:

This degree was determined by accurately counting the number of hairs fallen out after a sleep (of about 7 hours). As a result, hair falling decreased to about one third (about 10 hairs) in about one week. After a continuous application of one year, hair falling decreased to about one sixth (5 hairs).

Degree of growth in hair roots:

After one week from the commencement of application, the roots of fallen hairs began to exhibit a growth which was clear enough to be observed by the naked eye.

Degree of skin health:

The scalp color change into red at the time of drinking ceased to appear.

Blood circulation:

The blood circulation in the scalp was extremely improved, which improvement accompanied a sense of being tightly stretched in the scalp lasting for several hours. This seems to be attributable to the extention of vessels in the scalp. This sense continues to occur for several months to about one year after the commencement of application, but gradually ceases as the thickness of the scalp increases.

Scalp color:

The scalp got tinged with a blue color seen in the scalp of a healthy female.

Sensitivity in skin sensation:

Before the application, the subjects did not feel pain even when the scalp was picked with a needle. After the completion of the application, they began to feel pain sensitively.

Scalp thickness:

As a result of one year application, the scalp increased its thickness and became elastic. Due to these changes, the sense of oppression in the scalp at the time of application of the hair grower ceased.

From the above, it is concluded that the hair grower of the present invention activates trichogen cells, has an extremely excellent hair-growing effect, and produces remarkable effects which can achieve the object of the present invention.

EFFECT OF THE INVENTION

The hair grower of the present invention reactivates trichogen cells, stimulates the scalp through astriction upon trichogen cells and promotes blood circulation in the scalp, to thereby grow the subcutaneous tissues of the scalp and restore the initial scalp neuropil which reacts with stimulation properly. Thus, a strong hair-growing effect is achieved which will convert the downy hairs covering the part that lost hairs into initial, long and thick hairs.

What is claimed is:

1. A hair grower comprising as an active ingredient(s) one or more compounds selected from the group consisting of allantoin, derivatives thereof, compounds thereof and compounds of allantoin derivatives, said hair grower further comprising as an active ingredient(s) one or more compounds selected from aluminium compounds.

* * * * *